United States Patent [19]
Burkholder et al.

[11] 3,935,363
[45] Jan. 27, 1976

[54] ABSORBENT PRODUCT CONTAINING FLOCCULATED CLAY MINERAL AGGREGATES

[75] Inventors: Nelson D. Burkholder; Ralph L. Wisner, both of Midland, Mich.; Dudley A. Taber, The Hague, Netherlands

[73] Assignee: The Dow Chemical Company, Midland, Mich.

[22] Filed: Sept. 16, 1974

[21] Appl. No.: 506,364

[52] U.S. Cl. ............... 428/281; 428/454; 128/296; 128/284
[51] Int. Cl.² .......................................... B32B 9/00
[58] Field of Search.... 117/143 B, 144, 152, 169 A; 128/284, 290 R, 296; 210/41; 427/180, 430, 439; 428/281, 454

[56] References Cited
UNITED STATES PATENTS

| | | | |
|---|---|---|---|
| 2,388,616 | 11/1945 | LaLande | 210/41 |
| 2,434,418 | 1/1948 | LaLande | 210/41 |
| 2,750,944 | 6/1956 | Tollstrup | 128/290 R |
| 3,340,875 | 9/1967 | Dudley et al. | 128/290 R |
| 3,670,731 | 6/1972 | Harmon | 117/136 |

*Primary Examiner*—Cameron K. Weiffenbach
*Assistant Examiner*—Ralph E. Varndell, Jr.
*Attorney, Agent, or Firm*—Richard W. Hummer; H. Lyle Aamoth

[57] ABSTRACT

The difficulties in using clay minerals as absorbents in articles such as diapers, floor mats, utility wiping cloths, etc. is overcome by flocculating the clay into granular aggregates. The dry aggregates are dispersed into a flexible fibrous support to prepare the absorbent products. The aggregates, additionally, show enhanced water absorbing properties in many instances.

4 Claims, No Drawings

ABSORBENT PRODUCT CONTAINING FLOCCULATED CLAY MINERAL AGGREGATES

BACKGROUND

While clay minerals have been known as absorbents their use in absorbent articles such as diapers, floor mats, wiping cloths, etc. has been hampered by their natural tendency to form colloidal type dispersions in contact with aqueous solutions. Consequently, the clay rapidly migrates to the surface and can be readily washed out of the absorbent article. From an economic standpoint, clay minerals are ideally suited for throwaway (disposable) articles but their colloidal characteristics prevent their use in such articles.

SUMMARY OF THE INVENTION

This invention not only overcomes the natural tendency of clay minerals to form colloidal dispersions but also enhances their water absorbing properties in many cases.

Clay minerals may now be advantageously used in absorbent articles according to this invention by first flocculating a dispersion of the clay minerals into granular aggregates, separating the aggregate from the liquid and drying the aggregates. In this aggregate form the clay minerals retain their integrity when in contact with aqueous solutions and in addition are capable in many cases of holding more absorbed solution than the untreated clay. Consequently novel absorbent articles may be prepared having the clay mineral aggregates dispersed therein.

DESCRIPTION

Absorbent articles of various kinds may be made according to this invention. While it is possible to dry and reuse the article, the articles claimed herein are principally intended as disposable (throwaway) articles. Typical disposable absorbent articles include diapers, sanitary napkins, tampons, dressings, mats, wiping cloths and the like.

As previously pointed out, clay minerals are economically of interest in preparing absorbent articles since they are cheap, readily available and absorb aqueous liquids. Their colloidal, dispersive characteristics in the presence of such liquids, however, make clay minerals undesirable.

In the present invention clay minerals may be advantageously used for their water absorbing properites without their undesirable colloidal properties. This is accomplished by flocculating an aqueous dispersion of a clay mineral into aggregates, separating the aggregates from the liquid and drying same. The aggregates can be ground if desired. The flocculated aggregates are water stable, have enhanced water absorbing properties and can be dried and reused.

By clay minerals it is meant to include herein the hydrous silicates of aluminium, iron and magnesium which by mineralogical definition include the kaolin, montmorillonite, illite, vermiculite, glauconite, attapulgite and like clay minerals. These clay minerals are, characterized by extreme fineness of particle size, often colloidal in size. Certain montmorillonites, called bentonites, are preferred because of their greater water absorbing properties.

Dispersions of the clay minerals may be readily flocculated (aggregated) by introducing small amounts of polymeric materials such as polyacrylic acid, polyacrylamide, copolymers of acrylamide and acrylic acid, polyalkyleneamines, polyethylenimine, polystyrene sulfonate, polymers and copolymers of aminoalkyl acrylates and methacrylates and their ammonium and quaternary salts thereof. A large variety of polymeric flocculating agents are well known, e.g. see U.S. Pat. No. 2,687,374. In addition to polymeric agents it is also known to use inorganic salt solutions either alone or in conjunction with the polymeric agents. Typical inorganic salts include ferric salts, aluminium salts, calcium salts and the like.

Flocculation may also be enhanced by increasing the ionic strength of the water used to disperse the clay minerals. Tap water is preferred over distilled or deionized water, for example. Consequently the flocculation may be readily performed with most any available source of water.

After flocculation, the aggregate can be easily filtered to separate it from the aqueous solution. The aggregate is then dried and ground if considered necessary.

The present invention relates generally to absorbent articles and more particularly to disposable articles having dispersed therein dry, flocculated, water stable clay mineral aggregates which imbibe and hold several times their own weight of aqueous fluids. By flocculating (aggregating) the clay minerals they are converted into a form which is water stable and which resist the natural colloidal tendencies of the clay minerals. In addition enhanced water absorbing properties are produced in many instances.

One important use for the absorbent articles is to absorb body fluids and exudates, e.g. disposable diapers, sanitary napkins, tampons, dressings and the like. Another important use is as door mats to absorb water in entrance way areas or as wiping cloths for use in wiping counter tops, etc. and for other household, commercial or industrial purposes.

The absorbent article may be constructed in various forms such as by spreading the clay mineral aggregate as uniformly as possible onto or into a flexible fibrous support. The aggregate may be sandwiched between two or more of said fibrous supports. The same effect may be obtained by spreading the aggregate uniformly on a fibrous support and winding it on itself to form a roll so that the aggregate is confined between the windings. Numerous absorbent articles are disclosed in U.S. Pat. No. 3,670,731 and the latter is incorporated by reference herein to show the state of art with respect to the various configurations and constructions possible.

The absorbent article may have a water impermeable barrier film applied to one side of the article. Plastic films may completely envelope the article and have holes on one or both sides to allow aqueous fluids to penetrate into the article. The above are considered to be illustrative of the various kinds of articles which may be made but are not to be considered limiting.

The flexible, fibrous support may be a pad or batting of textile fibers, wood pulp fibers, cotton linters and mixtures of such fibers or one or more sheets of textile fibers, either synthetic or natural fibers or mixtures thereof. Generally it is preferred to use a fibrous support which itself is capable of absorbing aqueous solutions, e.g. cellulosic fibers such as wood pulp, cotton, etc. and hydrophillic synthetic fibers.

The efficacy of the present invention was illustrated by a simple comparative test where two diapers were made from a pad of cellulose fibers one containing an untreated clay mineral and one containing a flocculated (aggregated) clay mineral. In the first instance when the diaper was wetted with a 1.4% NaCl solution, the clay came to the surface when the diaper was pressed with the hand. However, in the second case the clay mineral aggregates held onto the fluid and did not migrate to the surface even when the diaper was pressed repeatedly.

The enhanced water holding capacity of the clay mineral aggregates was shown in another series of tests with a western bentonite clay (a montmorillonite) and an illite clay. The clays were separately dispersed in a 1.4% NaCl solution and flocculated by the addition of small amounts of a polyacrylamide flocculating agent. The flocculated clays were then filtered and the amount of absorbed solution determined. In similar manner untreated clays were dispersed, filtered and the amount of absorbed solution determined. The results are shown below.

The western bentonite clay was flocculated, as above, separated from the solution and dried. Upon reimmersing the flocculated bentonite in the sodium chloride solution it had an absorbency of 4.44 gms/gm of clay. This shows that the flocculated clay retains its absorbency after drying.

Further tests were made with three different clay minerals -- a kaolin, an atapulgite and a vermiculite. A weighed amount of each of the clays was dispersed and flocculated with an organic polymeric flocculant (an acrylamide, sodium acrylate copolymer). A second dispersion was flocculated with $CaCl_2$. The aggregates were filtered from the solution and the weight determined. The aggregates were then dried. The percent reswell was then measured by immersing the aggregates and determining the wet weight as before. The results are shown in the table.

In addition to diapers the flocculated clay mineral aggregates may be incorporated into other absorbent articles by dispersing them into a flexible fibrous support.

|  | Kaolin | | | Atapulgite | | | Vermiculite | | |
|---|---|---|---|---|---|---|---|---|---|
|  | C* | O* | I* | C | O | I | C | O | I |
| Dry Weight | 12.7 | 15.0 | 14.5 | 18.2 | 25.0 | 21.3 | 11.9 | 15.5 | 13.3 |
| Wet Weight | 17.2 | 20.8 | 28.2 | 42.4 | 50.2 | 46.2 | 17.2 | 28.8 | 21.5 |
| % Swell | 35 | 39 | 94 | 133 | 101 | 119 | 45 | 86 | 62 |
| Reswell Wet Weight | 17.7 | 20.5 | 18.2 | 28.1 | 30.7 | 35.3 | 15.6 | 23.0 | 17.8 |
| Reswell % | 39 | 37 | 26 | 54 | 23 | 66 | 31 | 48 | 34 |

*C - control (no flocculant)
O - organic flocculant aggregate
I - inorganic flocculant aggregate

| Absorbent | Absorbency |
|---|---|
| Illite Clay | 0.60 gms fluid/gm of clay |
| Flocculated Illite | 0.88 do |
| Western Bentonite | 3.70 do |
| Flocculated Bentonite | 4.59 do |

The above clays were added in the wet form to a diaper to determine if they had enough integrity to remain in the diaper. The unflocculated clays easily worked their way through the diaper to the outer surface whereas the flocculated clays did not migrate.

What is claimed is:
1. An article for absorbing aqueous fluids comprising a flexible fibrous support having dispersed therein dry, water stable, flocculated clay mineral aggregates.
2. The article of claim 1 wherein said support is cellulosic.
3. The article of claim 1 wherein the clay mineral is a montmorillonite.
4. The article of claim 1 wherein the clay mineral is a bentonite.

* * * * *